(12) United States Patent
Garvey et al.

(10) Patent No.: US 10,945,636 B2
(45) Date of Patent: Mar. 16, 2021

(54) TEMPERATURE BASED RESPIRATORY DETECTION

(71) Applicant: Worcester Polytechnic Institute, Worcester, MA (US)

(72) Inventors: Lucy Garvey, Westerly, RI (US); Lubna Hassan, Worcester, MA (US); Kyla Nichols, Pittsfield, MA (US); Allison Paquin, North Attleborough, MA (US); Robert J. Daniello, Florence, MA (US)

(73) Assignee: Worcester Polytechnic Institute, Worcester, MA (US)

( * ) Notice: Subject to any disclaimer, the term of this patent is extended or adjusted under 35 U.S.C. 154(b) by 188 days.

(21) Appl. No.: 15/916,628

(22) Filed: Mar. 9, 2018

(65) Prior Publication Data
US 2018/0256070 A1    Sep. 13, 2018

Related U.S. Application Data

(60) Provisional application No. 62/469,254, filed on Mar. 9, 2017.

(51) Int. Cl.
*A61B 5/08*    (2006.01)
*A61B 5/087*    (2006.01)
(Continued)

(52) U.S. Cl.
CPC ............ *A61B 5/0878* (2013.01); *A61B 5/085* (2013.01); *A61B 5/091* (2013.01); *A61B 5/0809* (2013.01);
(Continued)

(58) Field of Classification Search
CPC ....... A61B 5/087; A61B 5/0878; A61B 5/085; A61B 5/091; A61B 5/0809; A61B 5/1135;
(Continued)

(56) References Cited

U.S. PATENT DOCUMENTS 4,019,382 A * 4/1977 El-Gammal ......... A61B 5/0878
                                                73/861.39
5,676,132 A * 10/1997 Tillotson .............. A61B 5/0878
                                                128/204.23

(Continued)

OTHER PUBLICATIONS

International Search Report, PCT/US218/021691, dated Jun. 21, 2018, pp. 2.

*Primary Examiner* — Christian Jang
(74) *Attorney, Agent, or Firm* — Armis IP Law, LLC

(57) ABSTRACT

An equine respiratory detection device provides an inexpensive, portable appliance for evaluating equine health. A muzzle or mouthpiece attaches to the equine mouth region for sealably engaging with the respiratory pathway. The mouthpiece attached to a tubular vessel having a volumetric sensing apparatus for measuring respiratory inflow and outflow rates. The sensing apparatus includes a hot wire anemometer and sensing circuit for sensing flow rates based on changing electrical characteristics of a sensing element resulting from a temperature and humidity of the respiratory gases. Inhaling results in inflow gases having a cooling effect on a thermistor which affects the current flow in the sensor circuit. Similarly, exhaled outflow gases have increased temperature and humidity which allow identification of bidirectional flow and computation of an overall respiration volume to the equine patient subject.

8 Claims, 3 Drawing Sheets

(51) Int. Cl.
  *A61B 5/085* (2006.01)
  *A61B 5/091* (2006.01)
  *A61B 5/113* (2006.01)

(52) U.S. Cl.
  CPC ......... *A61B 5/1135* (2013.01); *A61B 2503/40* (2013.01); *A61B 2562/029* (2013.01); *A61B 2562/0271* (2013.01)

(58) Field of Classification Search
  CPC . A61B 5/097; A61B 5/746; A61B 2562/0271; A61B 2503/40; A61B 2562/029; A61M 16/0051; A61M 16/06; A61M 16/021; A61M 16/047; A61M 16/0841
  USPC ........................................ 600/537, 538, 543
  See application file for complete search history.

(56) References Cited

U.S. PATENT DOCUMENTS

| | | | |
|---|---|---|---|
| 6,287,264 B1 | 9/2001 | Hoffman | |
| 6,723,055 B2 | 4/2004 | Hoffman | |
| 6,952,912 B2 | 10/2005 | Lambert | |
| 7,094,206 B2 | 8/2006 | Hoffman | |
| 8,740,808 B2 * | 6/2014 | Curti | A61B 5/087 600/538 |
| 2002/0120207 A1 * | 8/2002 | Hoffman | A61B 5/0809 600/538 |
| 2004/0039295 A1 | 2/2004 | Olbrich | |
| 2004/0186390 A1 | 9/2004 | Lynette et al. | |

\* cited by examiner

TEMPERATURE BASED RESPIRATORY DETECTION

BACKGROUND

Equine lung function disorders are a recognized treatable ailment for stabled horses. Equine based industries such as racing, instruction and recreational riding depend on healthy horses. It has been estimated that as many as 80% of stabled horses may be suffering from some aspect of inflammatory airway disease. A majority of horses are housed in stables, which tend to be prone to poor air quality due to hay, dirt, and dust. Nonetheless, horses are part of a well-established industry; the horse racing industry generates an average of $1.2 million dollars from bets for each race in the United States. Activities such as horse racing or pulling both rely heavily on a functional equine respiratory system. This makes identification and treatment of pulmonary disorders a significant aspect of productive horse ownership.

SUMMARY

An equine respiratory detection device provides an inexpensive, portable appliance for evaluating equine health. A muzzle or mouthpiece attaches to the equine mouth region for sealably engaging with the respiratory pathway. The mouthpiece attaches to a tubular vessel having a volumetric sensing apparatus for measuring respiratory inflow and outflow rates. The sensing apparatus includes a hot wire anemometer and sensing circuit for sensing flow rates based on changing electrical characteristics of a sensing element resulting from a velocity, temperature and humidity of the respiratory gases. Inhaling results in inflow gases having a cooling effect on a thermistor which affects the current flow in the sensor circuit. Similarly, exhaled outflow gases have increased temperature and humidity which allows identification of bidirectional flow and computation of an overall respiration volume concerning the equine patient subject.

Configurations herein are based, in part, on the observation that equine respiratory health represents significant economic interests yet may not be readily examined or observed. A veterinary patient such as a horse cannot communicate poor health symptoms as a human can, and therefore it is only by proactive observation that ailments are detectable. Unfortunately, conventional approaches to equine respiration flow rates suffer from the shortcoming of requiring expensive equipment that is unwieldy for a traveling veterinarian to employ. Further, conventional approaches relying on strain gauge or pressure-based sensing may impede respiration due to flow restriction, skewing the results and imposing animal stress. Accordingly, configurations herein substantially overcome the above-described shortcomings by providing a portable, low cost volumetric flow device employing a temperature imposed variance in electrical characteristics of a sensing element. Flow rates are determined by the cooling effect on the sensing element, allowing unimpeded full respiratory throughput. Analysis includes both inflow and outflow directions based on volumetric computations, in contrast to conventional flow meters which expect continuous, unidirectional flow. The sensor element may be defined by a hot wire anemometry concept which effectively uses thermal sensing to measure airflow.

In further detail, the claimed approach depicts a device for detecting equine respiratory airflow that includes a tubular vessel adapted for fluidic communication with a respiratory source, and a sensor element disposed within a fluid path in the tubular vessel which is responsive to the respiratory source for receiving respiratory stimuli. The tubular device has a shaped receptacle at one end to fit around the mouth of the horse for capturing respiratory gases. A sensing circuit connects to the sensor element for monitoring electrical characteristics of the sensor element to determine a respiratory volume passing through the tubular vessel. The sensing circuit is adapted to detect an inflow and outflow rate of respiratory gases based on a temperature and humidity of the respiratory gases.

The disclosed device therefore performs a method of determining equine respiratory flow by disposing the tubular vessel around a breathing orifice of an equine patient, such that the tubular vessel is adapted to form a sealing engagement around the breathing orifice, based on a sensor element disposed therein. From the inhalation and exhalation patterns of the subject animal, the sensor circuit receives volumetric readings from the sensor element, in which the sensor element has variable electrical characteristics based on a temperature and humidity of respiratory gases flowing past the sensor element. The sensor circuit computes, based on a series of volumetric readings, the equine respiratory flow, in which the volumetric readings are defined by changes in electrical characteristics of the sensor element during inflow and outflow of respiratory gases of the equine patient. In a particular configuration, the sensor element includes a thermistor having an electrical resistance that varies with temperature, in which the temperature results from a volume of respiration gases passing through the tubular vessel from the respiration source. Other factors include detecting a reduced current through the sensor element in response to a cooling effect of the respiratory gases based on a temperature and humidity of the respiratory gases.

BRIEF DESCRIPTION OF THE DRAWINGS

The foregoing and other objects, features and advantages of the invention will be apparent from the following description of particular embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION

Configurations below depict an example equine respiratory detection device, which provides a volumetric flow detection for equine veterinary contexts in an inexpensive, portable form.

Figure 1:
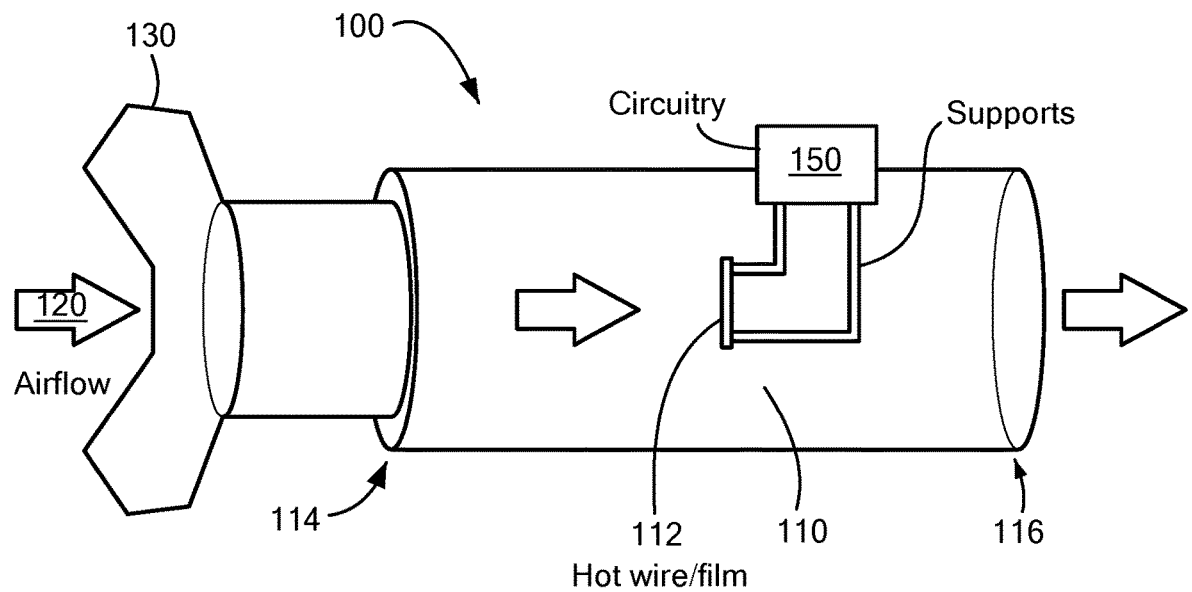
FIG. 1 is a perspective, transparent view of the equine respiratory detection and computation device as disclosed herein.

FIG. 1 is a perspective, transparent view of the equine respiratory detection and computation device as disclosed herein. Referring to FIG. 1, the device 100 for detecting equine respiratory airflow includes a tubular vessel 110 adapted for fluidic communication with a respiratory source such as a horse. A sensor element 112 is disposed within a fluid path 120 in the tubular vessel 110 and is responsive to the respiratory source for receiving respiratory stimuli. The tubular vessel 110 is adapted for sealable communication with an equine respiration system for directing inhaled and exhaled respiratory volume through the tubular vessel. A muzzle or mouthpiece 130 attaches to a proximate end 114 of the vessel 110 for directing the inflow and outflow (inhaled and exhaled) respiration gases. A distal end 116 is open for atmospheric communication and intake of fresh air. A sensing circuit 150 connects to the sensor element 112 and is operable for monitoring electrical characteristics of the sensor element 112 for determining a respiratory volume passing through the tubular vessel 110. The sensing circuit 150 is adapted to detect an inflow and outflow of respiratory gases based on a velocity, temperature and humidity of the respiratory gases, and may include multiple sensing elements 112, circuit elements or processing chips for detecting and isolating respective inflows and outflows for computing an accurate respiratory volume.

Figure 2:
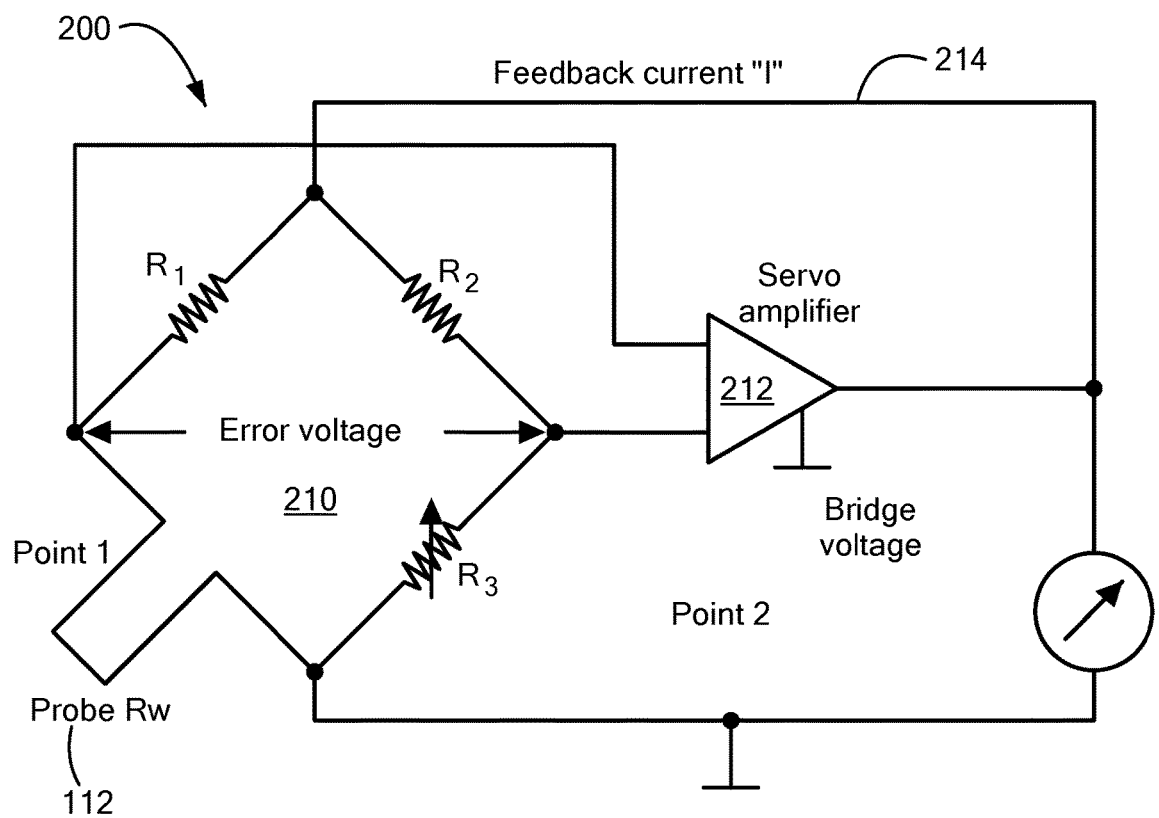
FIG. 2 is an example of a sensor circuit in the device of FIG. 1.

FIG. 2 is an example of a sensor circuit in the device of FIG. 1. Referring to FIGS. 1 and 2, the sensor element 112 and sensor circuit 150 may be fulfilled by a hot wire anemometer. The sensor element 112 is a thermistor or similar element such that the electrical characteristics vary with temperature. In the example shown, the sensor element 112 is a thermistor having an electrical resistance that varies with temperature, such that the temperature is based on a volume of respiration gases passing through the tubular vessel 110 to or from the respiration source as respiration gases are exchanged.

The hot wire anemometry approach, therefore, uses thermal sensing to measure airflow. Hot wire anemometers can be wires, meshes, or films; wires are often made of platinum, but tungsten, glass tubes, silicon films, and quartz wires can also be used. The material used should have a high temperature coefficient of resistance to increase sensitivity to velocity variations and an electrical resistance low enough that the wire can heat up at a reasonable voltage and current level. The material should also be strong enough to withstand stresses from flow velocities.

The resulting anemometer approach is a method of thermal sensing to measure airflow as a cost advantage over conventional approaches. Mass air flow sensors may be sourced which utilize a hot wire. A hot wire anemometers may also be fabricated using materials such as tungsten or platinum wire. Tungsten or platinum wire can also be readily sourced from chemical supply vendors. Thermistors can also be used to measure airflow by thermal sensing similar to hot wire anemometry when configured a specific way. A thermistor is a resistor whose resistance increases when cooled, such as from equine respiration (breath). A thermistor with accompanying embedded circuitry to measure air speed can also be readily sourced and implemented as a sensor element 212 in the disclosed anemometer.

It should therefore be apparent that several variations of the anemometer approach may be incorporated with appropriate sensing circuits. There are constant current and constant temperature hot wire anemometers. Constant temperature hot wires are used more frequently because they are an accepted standard, are easier to use, and produce lower noise. FIG. 2 shows one configuration of a circuit 200 used when building a constant temperature hot wire anemometer. The circuit design utilizes a Wheatstone bridge 210 to determine an unknown resistance. R1 and R2 are fixed resistors, R3 is a variable resistor, and Rw is the hot wire defining the sensor element 212. Rw completes the bridge and is a function of temperature. R3 adjusts to the Rw starting point. As airflows over Rw, the temperature, and therefore the resistance, change. The flow generates a voltage difference between points 1 and 2 which is recognized by an amplifier 212. The amplifier then adjusts the feedback current 214 to keep the wire temperature and resistance constant by rebalancing the bridge 210. Various alternate configurations and advancements have been made to hot wire anemometry in general. The sensors are generally reliable, sensitive, have a fast response time, and can be fabricated on a miniature scale to measure single point flow measurements. Configurations herein observe the feedback current 214 by the sensing circuit 150 in determination of the velocity, and in turn, the flow volume, through the vessel 110. The sensor element 112 may be fulfilled by a thermistor having a resistance that varies inversely with temperature, or alternatively varies other electrical characteristics.

Figure 3:
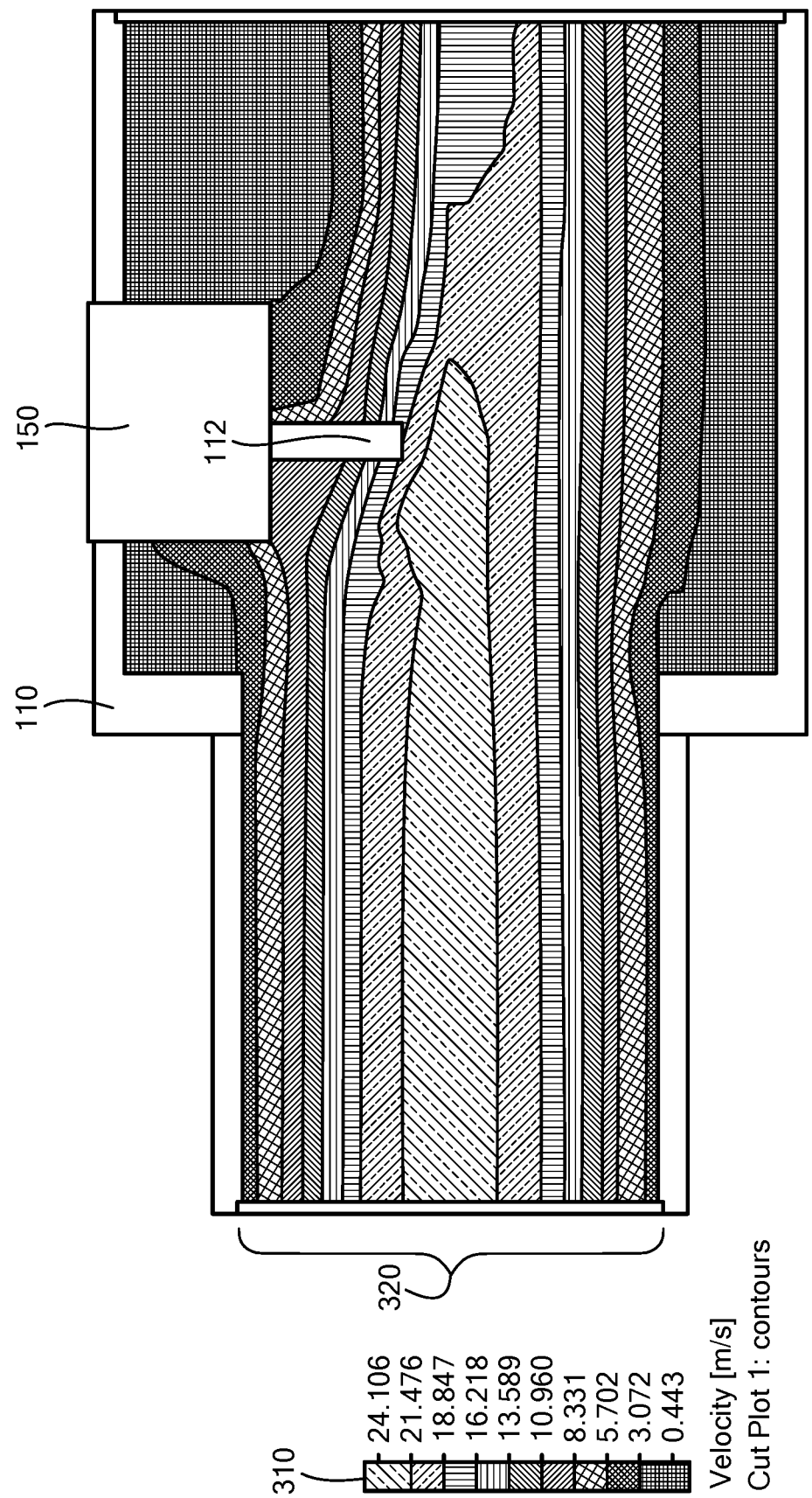
FIG. 3 is a graph of flow velocity across the sensor element in the device of FIG. 1.

FIG. 3 is a graph of flow velocity across the sensor element in the device of FIG. 1. The tubular vessel 110 and sensor element 112 are disposed in a noninterfering arrangement with the equine respiration system such that respiratory gases are unencumbered from passage. An interior size of the tubular vessel 110 is sufficiently large and the sensor element 112 sufficiently small that the device 100 does not interfere with or impede normal respiratory flow. In the graph of FIG. 3, velocity ranges 310 are depicted as regions 320 in the vessel 110.

Figure 4:
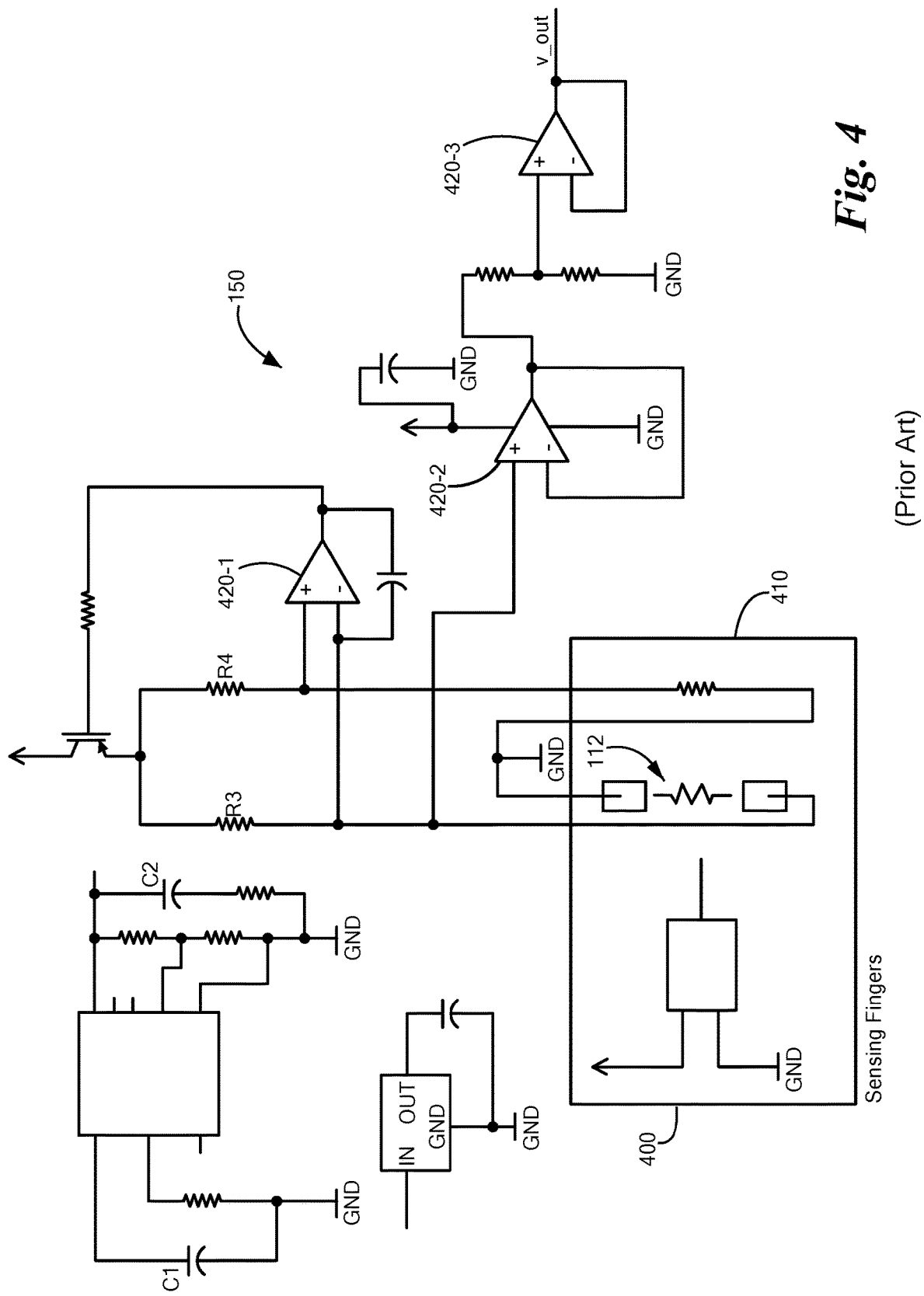
FIG. 4 is a more detailed example of the sensor circuit of FIG. 2.

FIG. 4 is a more detailed example of the sensor circuit of FIG. 2. Referring to FIGS. 2 and 4, the sensor element 112 is disposed in a sensing finger 410. The sensing finger 410 extends into the interior of the tubular vessel 110. Multiple sensing fingers 410 may be employed, for example to sense inflow and outflow conditions. A plurality of amplifiers 420-1 . . . 420-3 (420 generally) are employed to measure the current changes in response to temperature and hence, flow rate. Other circuit arrangements may be employed to generate an output electrical signal based on a sensor element 112 that varies electrical characteristics in response to temperature responsive to respiratory flow. In general, the sensing circuit 150 is operable to detect a reduced current through the sensor element 150 in response to a cooling effect of the respiratory gases based on a temperature and humidity of the respiratory gases. As the equine subject inhales and exhales, the respiratory flow has a cooling effect on the sensing element 112. Humidity also affects the cooling response, and hence the current through the sensing element 112. Exhalation exhausts moisture, and hence exhibits greater moisture content, or humidity. The sensor element 112 is therefore adapted to exhibit an increased resistance in response to cooling from the respiratory gases, and the sensing circuit 150 is operable to compute an outflow of respiratory gases based on an increased humidity in exhaled respiratory gases. In other words, sensing of the outflow recognizes and accommodates the increased humidity and corresponding temperature effect.

Conversely, the sensing circuit 150 is operable to determine a respiratory inflow based on a reduced humidity in inhaled respiratory volume, as the inhaled ambient fresh air has less moisture than the exhaled volume it is replacing. Multiple sensing elements, sensing circuits, or timing considerations are employed such that the sensing circuit 150 is operable to compute the respiratory volume based on computation of a bidirectional flow of respiratory gases through the tubular vessel 110.

In alternate configurations, the sensing circuit 150 further comprises an interface to a respiratory impedance plethysmography (RIP) band adapted to encircle an equine torso for abdominal expansion detection. Full respiration analysis includes airflow displacement as well as total volume. Diagnoses may include observation of the distribution of the inhaled air. The RIP bands around the torso and/or abdomen detect expansion, and operate in conjunction with the volume detection to identify the distribution within the body of the horse. This can identify locations of inflammation or blockage that impedes airflow within the anatomical regions of the horse.

While the system and methods defined herein have been particularly shown and described with references to embodiments thereof, it will be understood by those skilled in the art that various changes in form and details may be made therein without departing from the scope of the invention encompassed by the appended claims.

What is claimed is:

1. A device for detecting equine respiratory airflow, comprising:
    a straight tubular vessel having a mouthpiece having a stepped diameter adapted for sealable fluidic communication with a respiration source, the respiration source defined by an equine respiration system, the straight tubular vessel for directing inhaled and exhaled respiratory volume through the straight tubular vessel;
    a sensor element disposed in a noninterfering arrangement within a fluid path in the straight tubular vessel such that respiratory gases are unencumbered from passage, the sensor element responsive to the respiratory source for receiving respiratory stimuli; and
    a sensing circuit connected to the sensor element and operable for monitoring electrical characteristics of the sensor element for determining a respiratory volume passing through the straight tubular vessel, the sensing circuit adapted to detect an inflow and outflow of respiratory gases based on a temperature and humidity of the respiratory gases, the sensor element defined by a thermistor having a resistance that varies inversely with temperature, the temperature based on a volume of respiration gases passing through the tubular vessel from the respiration source.

2. The device of claim 1 wherein the sensing circuit is operable to detect a reduced current through the sensor element in response to a cooling effect of the respiratory gases based on a temperature and humidity of the respiratory gases.

3. The device of claim 2 wherein the sensor element is adapted to exhibit an increased resistance in response to cooling from the respiratory gases, and the sensing circuit is operable to compute an outflow of respiratory gases based on a difference in a sensed temperature resulting from increased humidity in exhaled respiratory gases.

4. The device of claim 3 wherein the sensing circuit is operable to determine a respiratory inflow based on a reduced humidity in inhaled respiratory volume.

5. The device of claim 2 wherein the sensing circuit is operable to compute the respiratory volume based on computation of a bidirectional flow of respiratory gases through the straight tubular vessel.

6. The device of claim 1 wherein the sensing circuit further comprises an interface to a respiratory impedance plethysmography (RIP) band adapted to encircle an equine torso for abdominal expansion detection.

7. A method of determining equine respiratory flow, comprising:
    disposing a mouthpiece coupled to a straight tubular vessel having a stepped diameter around a breathing orifice of an equine patient, the mouthpiece forming a sealing engagement around the breathing orifice, the straight tubular vessel having a sensor element disposed therein, the breathing orifice in fluidic communication with the mouthpiece for directing inhaled and exhaled respiratory volume through the straight tubular vessel via the mouthpiece;
    receiving, at a sensor circuit, volumetric readings from the sensor element, the sensor element disposed in a noninterfering arrangement within a fluid path in the straight tubular vessel such that respiratory gases are unencumbered from passage, and having variable electrical characteristics based on a temperature and humidity of respiratory gases flowing past the sensor element; and
    computing, based on a series of volumetric readings, the equine respiratory flow, the volumetric readings defined by changes in electrical characteristics of the sensor element during inflow and outflow of respiratory gases of the equine patient, the sensor element defined by a thermistor having a resistance that varies inversely with temperature, the temperature based on a volume of respiration gases passing through the tubular vessel from the respiration source.

8. The method of claim 7 further comprising detecting a reduced current through the sensor element in response to a cooling effect of the respiratory gases based on a temperature and humidity of the respiratory gases.

* * * * *